(12) United States Patent
Miller et al.

(10) Patent No.: US 8,609,920 B1
(45) Date of Patent: Dec. 17, 2013

(54) UZM-44 ALUMINOSILICATE ZEOLITE

(71) Applicant: UOP LLC, Des Plaines, IL (US)

(72) Inventors: Mark A. Miller, Niles, IL (US); Christopher P. Nicholas, Evanston, IL (US); Stephen T. Wilson, Libertyville, IL (US)

(73) Assignee: UOP LLC, Des Plaines, IL (US)

( * ) Notice: Subject to any disclaimer, the term of this patent is extended or adjusted under 35 U.S.C. 154(b) by 0 days.

(21) Appl. No.: 13/793,105

(22) Filed: Mar. 11, 2013

Related U.S. Application Data

(60) Provisional application No. 61/736,369, filed on Dec. 12, 2012.

(51) Int. Cl.
 *C07C 2/66* (2006.01)

(52) U.S. Cl.
 USPC .......................................... 585/467; 585/455

(58) Field of Classification Search
 USPC ................................. 585/467, 455
 See application file for complete search history.

(56) References Cited

U.S. PATENT DOCUMENTS

| | | | |
|---|---|---|---|
| 2,620,314 A | 12/1952 | Hoekstra | |
| 2,948,675 A | 8/1960 | Case et al. | |
| 3,146,188 A | 8/1964 | Gossett | |
| 3,227,645 A | 1/1966 | Frumkin et al. | |
| 3,658,695 A | 4/1972 | VanPool | |
| 3,839,187 A | 10/1974 | Vanvenrooy | |
| 4,197,192 A | 4/1980 | Gould | |
| 4,310,440 A | 1/1982 | Wilson et al. | |
| 4,354,928 A | 10/1982 | Audeh et al. | |
| 4,440,871 A | 4/1984 | Lok et al. | |
| 4,478,705 A | 10/1984 | Ganguli | |
| 4,483,691 A | 11/1984 | McShea, III et al. | |
| 4,645,589 A | 2/1987 | Krambeck et al. | |
| 4,870,222 A | 9/1989 | Bakas et al. | |
| 5,157,196 A | 10/1992 | Crossland et al. | |
| 5,157,197 A | 10/1992 | Cooper et al. | |
| 5,961,786 A | 10/1999 | Freel et al. | |
| 6,136,290 A | 10/2000 | Benazzi et al. | |
| 6,239,057 B1 | 5/2001 | Ichikawa et al. | |
| 6,426,442 B1 | 7/2002 | Ichikawa et al. | |
| 6,514,479 B1 | 2/2003 | Merlen et al. | |
| 6,613,302 B1 | 9/2003 | Moscoso et al. | |
| 6,627,781 B1 | 9/2003 | Briot et al. | |
| 6,740,788 B1 | 5/2004 | Maher et al. | |
| 6,756,030 B1 | 6/2004 | Rohde et al. | |
| 6,776,975 B2 | 8/2004 | Wilson et al. | |
| 6,982,074 B2* | 1/2006 | Jan et al. | 423/713 |
| 7,374,662 B2 | 5/2008 | Duplan et al. | |
| 7,419,931 B2 | 9/2008 | Serra et al. | |
| 7,575,737 B1 | 8/2009 | Miller et al. | |
| 7,615,143 B2 | 11/2009 | Chen et al. | |
| 7,629,499 B2 | 12/2009 | Serra Alfaro et al. | |
| 7,687,423 B2 | 3/2010 | Moscoso et al. | |
| 7,713,513 B2 | 5/2010 | Jan et al. | |
| 7,982,083 B2 | 7/2011 | Guillon et al. | |
| 8,048,403 B2 | 11/2011 | Miller et al. | |
| 8,134,037 B2 | 3/2012 | Bogdan et al. | |
| 8,178,740 B2 | 5/2012 | Nicholas et al. | |
| 8,183,172 B2 | 5/2012 | Guillon et al. | |
| 8,263,032 B2 | 9/2012 | Andersen et al. | |
| 8,398,955 B2 | 3/2013 | Lai et al. | |
| 8,461,405 B2 | 6/2013 | Sanchez et al. | |
| 2008/0179221 A1 | 7/2008 | Nguyen et al. | |
| 2010/0144513 A1 | 6/2010 | Nicholas et al. | |
| 2010/0144514 A1 | 6/2010 | Nicholas et al. | |
| 2010/0298117 A1 | 11/2010 | Levin et al. | |
| 2011/0174692 A1 | 7/2011 | Negiz et al. | |
| 2011/0178354 A1 | 7/2011 | Negiz et al. | |
| 2011/0178356 A1 | 7/2011 | Negiz et al. | |
| 2012/0024752 A1 | 2/2012 | Chen et al. | |
| 2012/0029257 A1 | 2/2012 | Chen et al. | |
| 2012/0121486 A1 | 5/2012 | Chen et al. | |

FOREIGN PATENT DOCUMENTS

| | | |
|---|---|---|
| CA | 2268803 A1 | 4/1998 |
| CN | 102040459 | 5/2011 |
| DE | 69710612 | 11/2002 |
| GB | 682387 | 11/1952 |
| GB | 915601 | 1/1963 |
| JP | 11253810 | 9/1999 |
| JP | 4595106 | 12/2010 |
| KR | 480229 | 3/2005 |
| KR | 2011047178 | 5/2011 |
| KR | 2012023156 | 3/2012 |
| KR | 1174099 | 8/2012 |

(Continued)

OTHER PUBLICATIONS

Hong et al., "Synthesis, Structure Solution, Characterization, and Catalytic Properties of TNU-10: A High-Silica Zeolite with the STI Topology", J. Am. Chem Society, 2004, vol. 126, pp. 5718-5826.

(Continued)

*Primary Examiner* — Thuan D Dang

(74) *Attorney, Agent, or Firm* — Maryann Maas

(57) ABSTRACT

A new family of aluminosilicate zeolites designated UZM-44 has been synthesized. These zeolites are represented by the empirical formula.

$$Na_nM_m^{k+}T_rAl_{1-x}E_xSi_yO_z$$

where "n" is the mole ratio of Na to (Al+E), M represents a metal or metals from zinc, Group 1, Group 2, Group 3 and or the lanthanide series of the periodic table, "m" is the mole ratio of M to (Al+E), "k" is the average charge of the metal or metals M, T is the organic structure directing agent or agents, and E is a framework element such as gallium. These zeolites are similar to IM-5 but are characterized by unique compositions and synthesis procedures and have catalytic properties for carrying out various hydrocarbon conversion processes and separation properties for carrying out various separations.

14 Claims, 3 Drawing Sheets

(56) References Cited

FOREIGN PATENT DOCUMENTS

| KR | 2012091865 | 8/2012 |
|---|---|---|
| WO | 9817581 | 4/1998 |
| WO | 2012027034 A2 | 3/2012 |

OTHER PUBLICATIONS

Gramm et al., "Complex zeolite structure solved by combining powder diffraction and electron microscopy", Nature, 2006, vol. 444, pp. 79-81.
Baerlocher et al., "Structure of Polycrystalline Zeolite Catalyst IM-5 Solved by Enhanced Charge Flipping", Science, 2007, vol. 315, pp. 1113-1116.
Rietveld, "A Profile Refinement Method for Nuclear and Magnetic Structures", Journal of Applied Crystallography, 1969, vol. 2, pp. 65-71.
Brunauer et al., "Adsorption of Gases in Multimolecular Layers", J. Am. Chem Society, 1938, vol. 60, pp. 309-319.
Portilla et al., "Structure-reactivity relationship for aromatics transalkylation and isomerization process with TNU-9, MCM-22 and ZSM-5 zeolites, and their industrial implications", Applied Catalysis A: General, 2011, vol. 393, n 1-2, pp. 257-268.
Serra et al., "A rational design of alkyl-aromatics dealkylation-transalkylation catalysts using C8 and C9 alkyl-aromatics as reactants", Journal of Catalysis, 2004, vol. 227, n. 2, pp. 459-469.
Cejka et al., "Novel zeolites in transformation of aromatic hydrocarbons", King Fand University of Petroleum and Minerals—18th Annual Saudi-Japan Symposium on Catalysts in Petroleum Refining and Petrochemicals, Nov. 2008, pp. 117-126, Publisher: King Fand Univ. of Petroleum and Minerals Res. Inst.
Bleken et al., "Conversion of methanol over 10-ring zeolites with differing vols. at channel intersections: Comparison of TNU-9, IM-5, ZSM-11 and ZSM-5w", Physical Chemistry Chemical Physics, 2011, vol. 13, n. 7, pp. 2539-2549.
Odedairo et al., "Toluene disproportionation and methylation over zeolites TNU-9, SSZ-33, ZSM-5, and mordenite using different reactor systems", Industrial and Engineering Chemistry Research, 2011, vol. 50, n. 6, pp. 3169-3183.
Corma et al., "IM-5: A highly thermal and hydrothermal shape-selective cracking zeolite", Journal of Catalysis, 2002, vol. 206, n. 1, pp. 125-133.
Jae et al., "Production of green aromatics from catalytic fast pyrolysis of lignocellulosic biomass", 11AIChE—2011 AIChE Annual Meeting, Conference Proceedings, Oct. 16-21, 2011, Publisher: American Institute of Chemical Engineers.
Jae et al., "Investigation into the shape selectivity of zeolite catalysts for biomass conversion", Journal of Catalysis, 2011, vol. 279, n. 2, pp. 257-268.
Tukur et al., "Comparison studies of xylene isomerization and disproportionation reactions between SSZ-33, TNU-9, mordenite and ZSM-5 zeolite catalysts", Chemical Engineering Journal, vol. 166, n. 1, pp. 348-357, Jan. 1, 2011.
Hong et al., "Synthesis, crystal structure, characterization, and catalytic properties of TNU-9", Journal of the American Chemical Society, 2007, vol. 129, n. 35, pp. 10870-10885.
Corma et al., "Determination of the pore topology of zeolite IM-5 by means of catalytic test reactions and hydrocarbon adsorption measurements", Journal of Catalysis, 2000, vol. 189, n. 2, pp. 382-394.
Lee et al., "Synthesis, characterization, and catalytic properties of zeolites IM-5 and NU-88", Journal of Catalysis, 2003, vol. 215, n. 1, pp. 151-170.
Palomares et al., "Co-exchanged IM5, a stable zeolite for the selective catalytic reduction of NO in the presence of water and SO2", Industrial and Engineering Chemistry Research, 2003, vol. 42, n. 8, pp. 1538-1542.
He et al., "A theoretical study of the stability of Cu2+ ion in IM-5 zeolite and the interaction of Cu-IM-5 with NO", Microporous and Mesoporous Materials, 2009, vol. 121, n. 1-3, pp. 95-102.
Liu et al., "Synthesis of Mo/TNU-9 (TNU-9 Taejon National University No. 9) catalyst and its catalytic performance in methane non-oxidative aromatization", Energy, 2011, vol. 36, n. 3, pp. 1582-1589.
Liu et al., "Synthesis of Mo/IM-5 catalyst and its catalytic behavior in methane non-oxidative aromatization", Fuel, 2011, vol. 90, n. 4, pp. 1515-1521.
Li et al., "Deep oxidative desulfurization of fuels in redox ionic liquids based on iron chloride", Green Chemistry, 2009, vol. 11, pp. 810-815.
Feng et al., "Application of phosphate ionic liquids in deep desulfurization of fuel", Petrochemical Technology, 2006, vol. 35, pp. 272-276.
Nie et al., "N, N-dialkylimidazolium dialkylphosphate ionic liquids: Their extractive performance for thiopene series compounds from fuel oils versus the length of alkyl group", Fuel Processing Technology, 2008, vol. 89, pp. 978-983.
U.S. Appl. No. 13/714,486, filed Dec. 14, 2012, Nicholas et al.
U.S. Appl. No. 13/714,539, filed Dec. 14, 2012, Nicholas et al.
U.S. Appl. No. 13/714,528, filed Dec. 14, 2012, Nicholas et al.
U.S. Appl. No. 13/714,504, filed Dec. 14, 2012, Nicholas et al.
U.S. Appl. No. 13/714,493, filed Dec. 14, 2012, Nicholas et al.
U.S. Appl. No. 13/793,047, filed Mar. 11, 2013, Miller et al.
U.S. Appl. No. 13/743,715, filed Jan. 17, 2013, Nicholas et al.
U.S. Appl. No. 13/792,879, filed Mar. 11, 2013, Nicholas et al.
U.S. Appl. No. 13/792,667, filed Mar. 11, 2013, Nicholas et al.
U.S. Appl. No. 13/792,610, filed Mar. 11, 2013, Nicholas et al.
U.S. Appl. No. 13/792,813, filed Mar. 11, 2013, Nicholas et al.

* cited by examiner

UZM-44 ALUMINOSILICATE ZEOLITE

CROSS REFERENCE TO RELATED APPLICATION

This application claims the benefit of priority of U.S. Provisional Application 61/736,369, filed Dec. 12, 2012, the contents of which are hereby incorporated by reference in its entirety.

FIELD OF THE INVENTION

This invention relates to a new family of aluminosilicate zeolites designated UZM-44. They are represented by the empirical formula of:

$$Na_n M_m^{k+} T_r Al_{1-x} E_x Si_y O_z$$

where M represents a metal or metals from zinc or Group 1 (IUPAC 1), Group 2 (IUPAC 2), Group 3 (IUPAC 3) or the lanthanide series of the periodic table, T is the organic directing agent or agents derived from reactants R and Q where R is an A,Ω-dihalosubstituted alkane such as 1,5-dibromopentane and Q is at least one neutral amine having 6 or fewer carbon atoms such as 1-methylpyrrolidine. E is a framework element such as gallium.

BACKGROUND OF THE INVENTION

Zeolites are crystalline aluminosilicate compositions which are microporous and which are formed from corner sharing $AlO_2$ and $SiO_2$ tetrahedra. Numerous zeolites, both naturally occurring and synthetically prepared, are used in various industrial processes. Synthetic zeolites are prepared via hydrothermal synthesis employing suitable sources of Si, Al and structure directing agents such as alkali metals, alkaline earth metals, amines, or organoammonium cations. The structure directing agents reside in the pores of the zeolite and are largely responsible for the particular structure that is ultimately formed. These species balance the framework charge associated with aluminum and can also serve as space fillers. Zeolites are characterized by having pore openings of uniform dimensions, having a significant ion exchange capacity, and being capable of reversibly desorbing an adsorbed phase which is dispersed throughout the internal voids of the crystal without significantly displacing any atoms which make up the permanent zeolite crystal structure. Zeolites can be used as catalysts for hydrocarbon conversion reactions, which can take place on outside surfaces as well as on internal surfaces within the pore.

A particular zeolite, IM-5, was first disclosed by Benazzi, et al. in 1996 (FR96/12873; WO98/17581) who describe the synthesis of IM-5 from the flexible dicationic structure directing agent, 1,5-bis(N-methylpyrrolidinium)pentane dibromide or 1,6-bis(N-methylpyrrolidinium)hexane dibromide in the presence of sodium. After the structure of IM-5 was solved by Baerlocher et al. (Science, 2007, 315, 113-6), the International Zeolite Structure Commission gave the code of IMF to this zeolite structure type, see Atlas of Zeolite Framework Types. The IMF structure type was found to contain three mutually orthogonal sets of channels in which each channel is defined by a 10-membered ring of tetrahedrally coordinated atoms, however, connectivity in the third dimension is interrupted every 2.5 nm, therefore diffusion is somewhat limited. In addition, multiple different sizes of 10-membered ring channels exist in the structure.

Applicants have successfully prepared a new family of materials designated UZM-44. The topology of the materials is similar to that observed for IM-5. The materials are prepared via the use of a mixture of simple commercially available structure directing agents, such as 1,5-dibromopentane and 1-methylpyrrolidine.

SUMMARY OF THE INVENTION

As stated, the present invention relates to a new aluminosilicate zeolite designated UZM-44. Accordingly, one embodiment of the invention is a material having a three-dimensional framework of at least $AlO_2$ and $SiO_2$ tetrahedral units and an empirical composition in the as synthesized and anhydrous basis expressed by an empirical formula of:

$$Na_n M_m^{k+} T_r Al_{1-x} E_x Si_y O_z$$

where "n" is the mole ratio of Na to (Al+E) and has a value from approximately 0.05 to 0.5, M represents at least one metal selected from the group consisting of zinc, Group 1 (IUPAC 1), Group 2 (IUPAC 2), Group 3 (IUPAC 3), and the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having 5 carbon atoms and Q is at least one neutral monoamine having 6 or fewer carbon atoms, "t" is the mole ratio of N from the organic structure directing agent or agents to (Al+E) and has a value of from about 0.5 to about 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

Another embodiment of the invention is a microporous crystalline zeolite having a three-dimensional framework of at least $AlO_2$ and $SiO_2$ tetrahedral units and an empirical composition in the as synthesized and anhydrous basis expressed by an empirical formula of:

$$Na_n M_m^{k+} T_r Al_{1-x} E_x Si_y O_z$$

where "n" is the mole ratio of Na to (Al+E) and has a value from approximately 0.05 to 0.5, M represents a metal or metals from Group 1 (IUPAC 1), Group 2 (IUPAC 2), Group 3 (IUPAC 3), the lanthanide series of the periodic table or zinc, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having 5 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of O to (Al+E) and has a value determined by the equation:

$$z=(n+k \cdot m+3+4 \cdot y)/2$$

and the zeolite is characterized in that it has the x-ray diffraction pattern having at least the d-spacings and intensities set forth in Table A. The zeolite is thermally stable up to a temperature of greater than 600° C. in one embodiment and at least 800° C. in another embodiment.

Another embodiment of the invention is a process for preparing the crystalline microporous zeolite described above. The process comprises forming a reaction mixture containing reactive sources of Na, R, Q, Al, Si and optionally E and/or M and heating the reaction mixture at a temperature of about 160° C. to about 180° C., or about 165° C. to about 175° C., for a time sufficient to form the zeolite. The reaction mixture has a composition expressed in terms of mole ratios of the oxides of:

a–b Na$_2$O:bM$_{n/2}$O:cRO:dQ:1-eAl$_2$O$_3$:eE$_2$O$_3$:fSiO$_2$:gH$_2$O where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000.

With this number of reactive reagent sources, many orders of addition can be envisioned. Typically, the aluminum reagent is dissolved in the sodium hydroxide prior to adding the silica reagents. Reagents R and Q can be added together or separately in many different orders of addition.

Yet another embodiment of the invention is a hydrocarbon conversion process using the above-described zeolite. The process comprises contacting the hydrocarbon with the zeolite at conversion conditions to give a converted hydrocarbon. Still another embodiment of the invention is a separation process using the above-described zeolite.

DETAILED DESCRIPTION OF THE INVENTION

Figure 1:
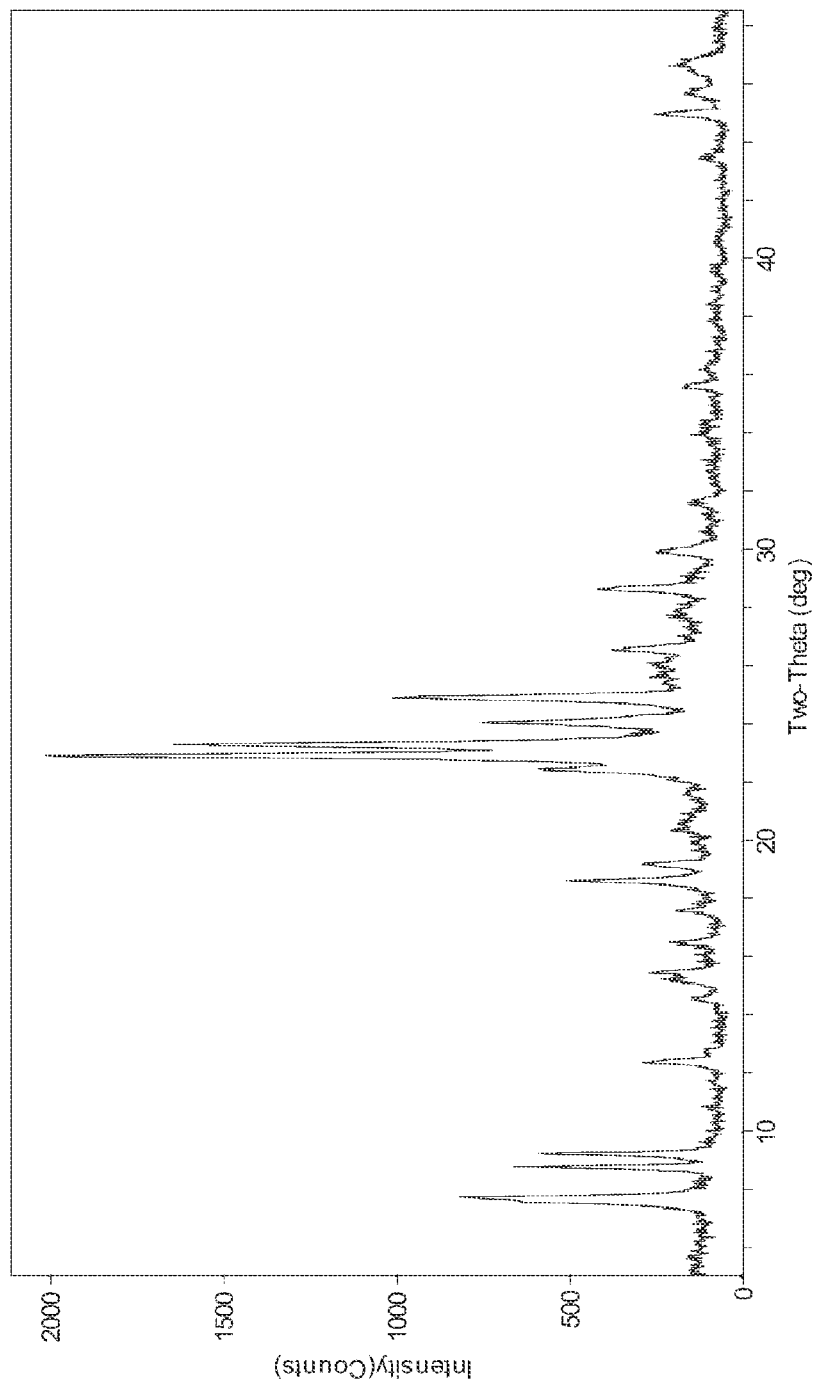
FIG. 1 is an XRD pattern of the UZM-44 zeolite formed in Example 1. This pattern shows the UZM-44 zeolite in the as-synthesized form.
Figure 2:
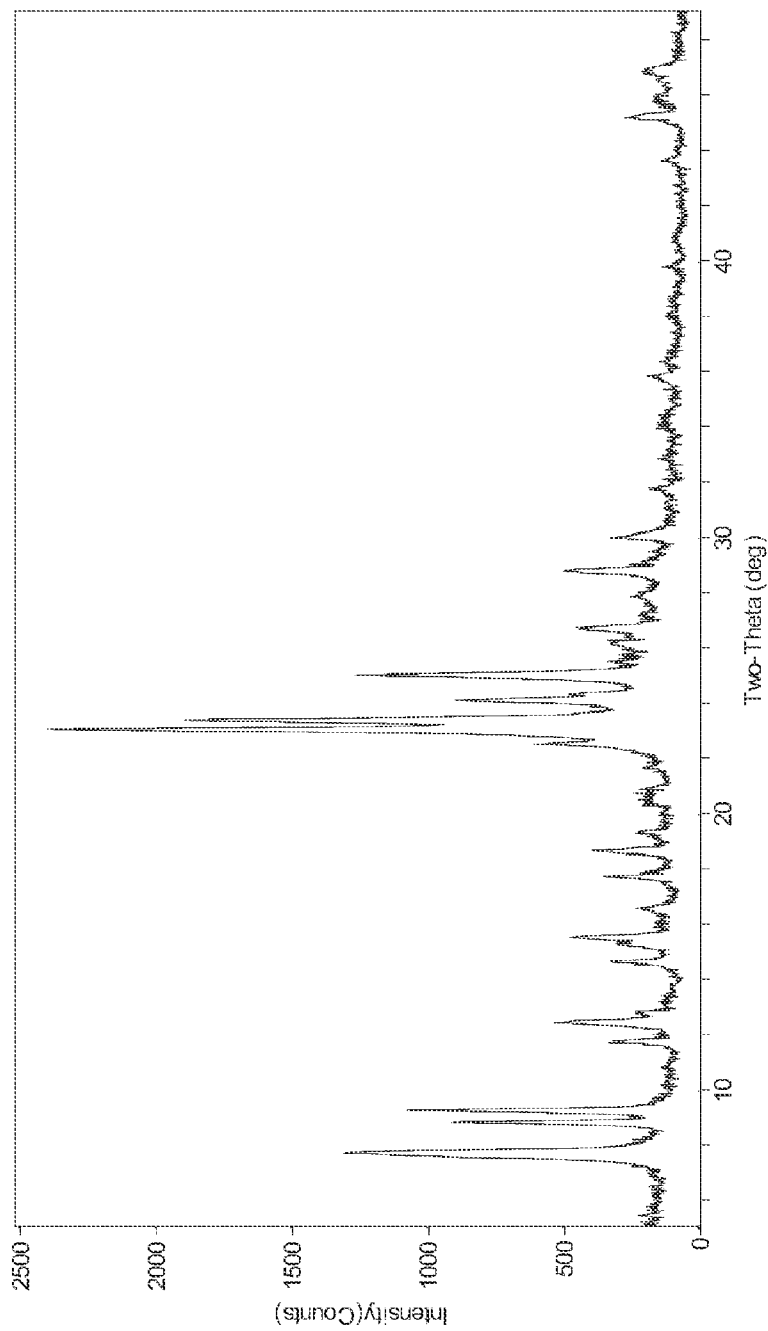
FIG. 2 is also an XRD pattern of the UZM-44 zeolite formed in Example 1. This pattern shows the UZM-44 zeolite in the H$^+$ form.

Applicants have prepared an aluminosilicate zeolite whose topological structure is related to IMF as described in Atlas of Zeolite Framework Types, which is maintained by the International Zeolite Association Structure Commission at http://www.iza-structure.org/databases/, the member of which has been designated IM-5. As will be shown in detail, UZM-44 is different from IM-5 in a number of its characteristics including its micropore volume. The instant microporous crystalline zeolite, UZM-44, has an empirical composition in the as synthesized and anhydrous basis expressed by an empirical formula of:

where "n" is the mole ratio of Na to (Al+E) and has a value from approximately 0.05 to 0.5, M represents a metal or metals selected from the group consisting of zinc, Group 1 (IUPAC 1), Group 2 (IUPAC 2), Group 3 (IUPAC 3), the lanthanide series of the periodic table, and any combination thereof, "m" is the mole ratio of M to (Al+E) and has a value from 0 to 0.5, "k" is the average charge of the metal or metals M, T is the organic structure directing agent or agents derived from reactants R and Q where R is an A,Ω-dihalogen substituted alkane having 5 carbon atoms and Q is at least one neutral monoamine having 6 or fewer carbon atoms, "t" is the mole ratio of N from the organic structure directing agent or agents to (Al+E) and has a value of from 0.5 to 1.5, E is an element selected from the group consisting of gallium, iron, boron and combinations thereof, "x" is the mole fraction of E and has a value from 0 to about 1.0, "y" is the mole ratio of Si to (Al+E) and varies from greater than 9 to about 25 and "z" is the mole ratio of 0 to (Al+E) and has a value determined by the equation:

$$z=(n+k\cdot m+3+4\cdot y)/2$$

Where M is only one metal, then the weighted average valence is the valence of that one metal, i.e. +1 or +2. However, when more than one M metal is present, the total amount of:

$$M_m{}^{k+}=M_{m1}{}^{(k1)+}+M_{m2}{}^{(k2)+}+M_{m3}{}^{(k3)+}+M_{m4}{}^{(k4)+}$$

and the weighted average valence "k" is given by the equation:

$$k = \frac{m1 \cdot k1 + m2 \cdot k2 + m3 \cdot k3 \ldots}{m1 + m2 + m3 \ldots}$$

In one embodiment, the microporous crystalline zeolite, UZM-44, is synthesized by a hydrothermal crystallization of a reaction mixture prepared by combining reactive sources of sodium, organic structure directing agent or agents T, aluminum, silicon, and optionally E, M, or both. The reaction mixture does not comprise seeds of a layered material L. The sources of aluminum include but are not limited to aluminum alkoxides, precipitated aluminas, aluminum metal, aluminum hydroxide, sodium aluminate, aluminum salts and alumina sols. Specific examples of aluminum alkoxides include, but are not limited to aluminum sec-butoxide and aluminum ortho isopropoxide. Sources of silica include but are not limited to tetraethylorthosilicate, colloidal silica, precipitated silica and alkali silicates. Sources of sodium include but are not limited to sodium hydroxide, sodium bromide, sodium aluminate, and sodium silicate.

T is the organic structure directing agent or agents derived from reactants R and Q where R is an A,Ω-dihalogen substituted alkane having 5 carbon atoms and Q comprises at least one neutral monoamine having 6 or fewer carbon atoms. R may be an A,Ω-dihalogen substituted alkane having 5 carbon atoms selected from the group consisting of 1,5-dichloropentane, 1,5-dibromopentane, 1,5-diiodopentane, and combinations thereof. Q comprises at least one neutral monoamine having 6 or fewer carbon atoms such as 1-ethylpyrrolidine, 1-methylpyrrolidine, 1-ethylazetidine, 1-methylazetidine, triethylamine, diethylmethylamine, dimethylethylamine, trimethylamine, dimethylbutylamine, dimethylpropylamine, dimethylisopropylamine, methylethylpropylamine, methylethylisopropylamine, dipropylamine, diisopropylamine, cyclopentylamine, methylcyclopentylamine, hexamethyleneimine. Q may comprise combinations of multiple neutral monoamines having 6 or fewer carbon atoms.

M represents at least one exchangeable cation of a metal or metals from Group 1 (IUPAC 1), Group 2 (IUPAC 2), Group 3 (IUPAC 3) or the lanthanide series of the periodic table and or zinc. Specific examples of M include but are not limited to lithium, potassium, rubidium, cesium, magnesium, calcium, strontium, barium, zinc, yttrium, lanthanum, gadolinium, and mixtures thereof. Reactive sources of M include, but are not limited to, the group consisting of halide, nitrate, sulfate, hydroxide, or acetate salts. E is an element selected from the group consisting of gallium, iron, boron and combinations thereof, and suitable reactive sources include, but are not limited to, boric acid, gallium oxyhydroxide, gallium nitrate, gallium sulfate, ferric nitrate, ferric sulfate, ferric chloride and mixtures thereof.

The reaction mixture containing reactive sources of the desired components can be described in terms of molar ratios of the oxides by the formula:

a–b Na$_2$O:bM$_{n/2}$O:cRO:dQ:1-eAl$_2$O$_3$:eE$_2$O$_3$:fSiO$_2$:gH$_2$O where "a" has a value of about 10 to about 30, "b" has a value of 0 to about 30, "c" has a value of about 1 to about 10, "d" has a value of about 2 to about 30, "e" has a value of 0 to about 1.0, "f" has a value of about 30 to about 100, "g" has a value of about 100 to about 4000.

The examples demonstrate specific orders of addition for the reaction mixture which leads to UZM-44. However, as there are at least 6 starting materials, many orders of addition are possible. Also, if alkoxides are used, it is preferred to include a distillation or evaporative step to remove the alcohol hydrolysis products. While the organic structure directing agents R and Q can be added separately or together to the reaction mixture at a number of points in the process, it is preferred to mix R and Q together at room temperature and add the combined mixture to a cooled mixture of reactive Si, Al and Na sources maintained at 0-10° C. Alternatively, the mixture of R and Q, after mixing at room temperature, could be cooled and the reactive sources of Si, Al, and Na added to the organic structure directing agent mixture while maintaining a temperature of 0-10° C. In an alternative embodiment, the reagents R and Q could be added, separately or together, to the reaction mixture at room temperature.

The reaction mixture is then reacted at a temperature of about 160° C. to about 180° C., or about 165° C. to about 175° C., for a period of about 1 day to about 3 weeks and preferably for a time of about 3 days to about 14 days in a stirred, sealed reaction vessel under autogenous pressure. Static crystallization does not yield UZM-44. After crystallization is complete, the solid product is isolated from the heterogeneous mixture by means such as filtration or centrifugation, and then washed with deionized water and dried in air at ambient temperature up to about 100° C.

The as-synthesized UZM-44 is characterized by the x-ray diffraction pattern, having at least the d-spacings and relative intensities set forth in Table A below. Diffraction patterns herein were obtained using a typical laboratory powder diffractometer, utilizing the K$_\alpha$ line of copper; Cu K alpha. From the position of the diffraction peaks represented by the angle 2theta, the characteristic interplanar distances d$_{hkl}$ of the sample can be calculated using the Bragg equation. The intensity is calculated on the basis of a relative intensity scale attributing a value of 100 to the line representing the strongest peak on the X-ray diffraction pattern, and then: very weak (vw) means less than 5; weak (w) means less than 15; medium (m) means in the range 15 to 50; strong (s) means in the range 50 to 80; very strong (vs) means more than 80. Intensities may also be shown as inclusive ranges of the above. The X-ray diffraction patterns from which the data (d spacing and intensity) are obtained are characterized by a large number of reflections some of which are broad peaks or peaks which form shoulders on peaks of higher intensity. Some or all of the shoulders may not be resolved. This may be the case for samples of low crystallinity, of particular coherently grown composite structures or for samples with crystals which are small enough to cause significant broadening of the X-rays. This can also be the case when the equipment or operating conditions used to produce the diffraction pattern differ significantly from those used in the present case.

The X-ray diffraction pattern for UZM-44 contains many peaks; an example of the x-ray diffraction patterns for an as-synthesized UZM-44 product is shown in FIG. 1. Those peaks characteristic of UZM-44 are shown in Table A. Additional peaks, particularly those of very weak intensity, may also be present. All peaks of medium or higher intensity present in UZM-44 are represented in Table A.

The zeolite may be further characterized by the x-ray diffraction pattern having at least the d-spacings and intensities set forth in Table A.

TABLE A

| 2-Theta | d(t) | I/Io % |
|---|---|---|
| 7.72 | 11.45 | m |
| 8.88 | 9.95 | m |
| 9.33 | 9.47 | m |
| 12.47 | 7.09 | w-m |
| 12.85 | 6.88 | vw |
| 14.62 | 6.05 | vw-w |
| 15.27 | 5.80 | w |
| 15.57 | 5.68 | w |
| 16.60 | 5.34 | w |
| 17.70 | 5.01 | vw-w |
| 18.71 | 4.74 | w-m |
| 19.30 | 4.59 | w |
| 22.55 | 3.94 | m |
| 23.03 | 3.86 | vs |
| 23.39 | 3.80 | s |
| 24.17 | 3.68 | m |
| 25.01 | 3.56 | m |
| 26.19 | 3.40 | vw-w |
| 26.68 | 3.34 | w-m |
| 28.76 | 3.10 | w-m |
| 30.07 | 2.97 | w |
| 35.72 | 2.51 | vw-w |
| 45.08 | 2.01 | w |
| 45.83 | 1.98 | vw-w |
| 46.77 | 1.94 | vw-w |

As will be shown in detail in the examples, the UZM-44 material is thermally stable up to a temperature of at least 600° C. and in another embodiment, up to at least 800° C. Also as shown in the examples, the UZM-44 material may have a micropore volume as a percentage of total pore volume of less than 60%.

Characterization of the UZM-44 product by high-resolution scanning electron microscopy shows that the UZM-44 forms in lathes which assemble into rectangular rod colonies.

As synthesized, the UZM-44 material will contain some exchangeable or charge balancing cations in its pores. These exchangeable cations can be exchanged for other cations, or in the case of organic cations, they can be removed by heating under controlled conditions. It is also possible to remove some organic cations from the UZM-44 zeolite directly by ion exchange. The UZM-44 zeolite may be modified in many ways to tailor it for use in a particular application. Modifications include calcination, ion-exchange, steaming, various acid extractions, ammonium hexafluorosilicate treatment, or any combination thereof, as outlined for the case of UZM-4M in U.S. Pat. No. 6,776,975 B1 which is incorporated by reference in its entirety. Conditions may be more severe than shown in U.S. Pat. No. 6,776,975. Properties that are modified include porosity, adsorption, Si/Al ratio, acidity, thermal stability, and the like.

After calcination, ion-exchange and calcination and on an anhydrous basis, the microporous crystalline zeolite UZM-44 has a three-dimensional framework of at least AlO$_2$ and SiO$_2$ tetrahedral units and an empirical composition in the hydrogen form expressed by an empirical formula of

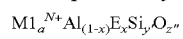

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

In the hydrogen form, after calcination, ion-exchange and calcination to remove $NH_3$, UZM-44 displays the x-ray diffraction pattern having at least the d-spacings and intensities set forth in Table B. Those peaks characteristic of UZM-44 are shown in Tables B. Additional peaks, particularly those of very weak intensity, may also be present. All peaks of medium or higher intensity present in UZM-44 are indicated in Table B.

TABLE B

| 2-Theta | d(t) | I/Io % |
|---|---|---|
| 7.71 | 11.47 | m-s |
| 8.84 | 10.00 | m-s |
| 9.24 | 9.56 | m |
| 11.76 | 7.52 | vw-w |
| 12.46 | 7.10 | m |
| 14.38 | 6.15 | vw |
| 14.64 | 6.05 | w |
| 15.26 | 5.80 | w |
| 15.52 | 5.70 | w-m |
| 16.58 | 5.34 | w |
| 17.72 | 5.00 | w-m |
| 18.64 | 4.76 | w |
| 22.56 | 3.94 | w-m |
| 23.06 | 3.85 | vs |
| 23.40 | 3.80 | s |
| 24.12 | 3.69 | m |
| 25.06 | 3.55 | m |
| 26.16 | 3.40 | vw-w |
| 26.74 | 3.33 | w-m |
| 28.82 | 3.10 | w-m |
| 30.12 | 2.96 | w |
| 35.86 | 2.50 | vw-w |
| 45.32 | 2.00 | w |
| 46.05 | 1.97 | vw-w |
| 46.92 | 1.93 | vw-w |

Similar to the as-synthesized material, the modified UZM-44 materials are thermally stable up to a temperature of at least 600° C. and in another embodiment, up to at least 800° C. and may have a micropore volume as a percentage of total pore volume of less than 60%.

Figure 3:
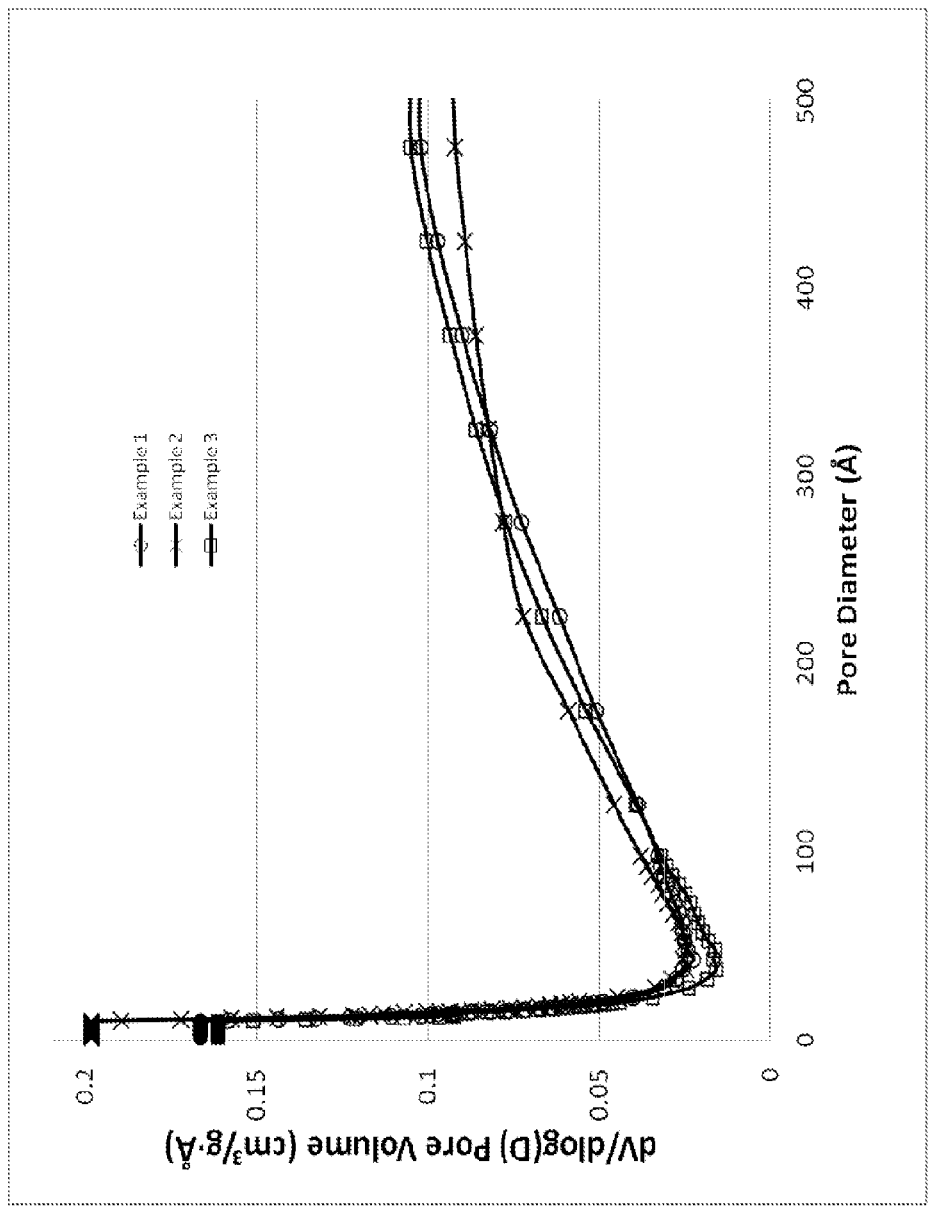
FIG. 3 is a plot derived from the N$_2$ BET experiment where dV/dlog(D) is plotted against the pore diameter. This plot shows the incremental amount of nitrogen adsorbed at each pore diameter measured.

Surface area, micropore volume and total pore volume may be determined, for example, by $N_2$ adsorption using the conventional BET method of analysis (J. Am. Chem. Soc., 1938, 60, 309-16) coupled with t-plot analysis of the adsorption isotherm as implemented in Micromeritics ASAP 2010 software. The t-plot is a mathematical representation of multilayer adsorption and allows determination of the amount of $N_2$ adsorbed in the micropores of the zeolitic material under analysis. In particular, for the materials described herein, points at 0.45, 0.50, 0.55, 0.60, and 0.65 $P/P_0$ are used to determine the slope of the t-plot line, the intercept of which is the micropore volume. Total pore volume is determined at 0.98 $P/P_0$. The UZM-44 of the instant invention has a micropore volume of less than 0.155 mL/g, typically less than 0.15 mL/g, and often less than 0.145 mL/g. Additionally, by looking at the dV/dlog D versus pore diameter plot (the differential volume of nitrogen adsorbed as a function of pore diameter), as shown in FIG. 3, the UZM-44 of the instant invention contains no feature at around 200-300 Å. As can be seen in FIG. 3, the material of Example 2, not in accordance with the invention, does contain a feature at around 200-300 Å. Instead, UZM-44 has an adsorption feature occurring at greater than 450 Å. In an embodiment, greater than 0.1 mL $N_2$/gÅ is differentially adsorbed at a pore diameter of 475 Å. Preferably, greater than 0.1 mL $N_2$/gÅ is differentially adsorbed at pore diameters greater than 475 Å where differentially adsorbed indicates the differential volume of nitrogen adsorbed at a particular pore diameter.

In specifying the proportions of the zeolite starting material or adsorption properties of the zeolite product and the like herein, the "anhydrous state" of the zeolite will be intended unless otherwise stated. The term "anhydrous state" is employed herein to refer to a zeolite substantially devoid of both physically adsorbed and chemically adsorbed water.

The crystalline UZM-44 zeolite of this invention can be used for separating mixtures of molecular species, removing contaminants through ion exchange and catalyzing various hydrocarbon conversion processes. Separation of molecular species can be based either on the molecular size (kinetic diameter) or on the degree of polarity of the molecular species.

The UZM-44 zeolite of this invention can also be used as a catalyst or catalyst support in various hydrocarbon conversion processes. Hydrocarbon conversion processes are well known in the art and include cracking, hydrocracking, alkylation of aromatics or isoparaffins, isomerization of paraffins, olefins, or poly-alkylbenzenes such as xylene, trans-alkylation of poly-alkybenzene with benzene or mono-alkybenzene, disproportionation of mono-alkybenzene, polymerization, reforming, hydrogenation, dehydrogenation, transalkylation, dealkylation, hydration, dehydration, hydrotreating, hydrodenitrogenation, hydrodesulfurization, methanation and syngas shift process. Specific reaction conditions and the types of feeds which can be used in these processes are set forth in U.S. Pat. No. 4,310,440 and U.S. Pat. No. 4,440,871 which are hereby incorporated by reference. Preferred hydrocarbon conversion processes are those in which hydrogen is a component such as hydrotreating or hydrofining, hydrogenation, hydrocracking, hydrodenitrogenation, hydrodesulfurization, etc.

Hydrocracking conditions typically include a temperature in the range of about 204° C. to about 649° C. (400° to 1200° F.) or about 316° C. to about 510° C. (600° F. and 950° F.). Reaction pressures are in the range of atmospheric to about 24,132 kPa g (3,500 psig), or between about 1379 to about 20,685 kPa g (200 to 3000 psig). Contact times usually correspond to liquid hourly space velocities (LHSV) in the range of about 0.1 $hr^{-1}$ to 15 $hr^{-1}$, preferably between about 0.2 and 3 $hr^{-1}$. Hydrogen circulation rates are in the range of 178 to about 8,888 std. $m^3/m^3$ (1,000 to 50,000 standard cubic feet (scf) per barrel of charge), or about 355 to about 5,333 std. $m^3/m^3$ (about 2,000 to about 30,000 scf per barrel of charge). Suitable hydrotreating conditions are generally within the broad ranges of hydrocracking conditions set out above.

The reaction zone effluent is normally removed from the catalyst bed, subjected to partial condensation and vapor-liquid separation and then fractionated to recover the various components thereof. The hydrogen, and if desired some or all of the unconverted heavier materials, are recycled to the reactor. Alternatively, a two-stage flow may be employed with the unconverted material being passed into a second reactor.

Catalysts of the subject invention may be used in just one stage of such a process or may be used in both reactor stages.

Catalytic cracking processes are preferably carried out with the UZM-44 composition using feedstocks such as gas oils, heavy naphthas, deasphalted crude oil residua, etc. with gasoline being the principal desired product. Temperature conditions of about 454° C. to about 593° C. (about 850° F. to about 1100° F.), LHSV values of 0.5 to 10 and pressure conditions of from about 0 to about 344 kPa g (about 0 to 50 psig) are suitable.

Alkylation of aromatics usually involves reacting an aromatic ($C_2$ to $C_{12}$), especially benzene, with a monoolefin to produce a linear alkyl substituted aromatic. The process is carried out at an aromatic:olefin (e.g., benzene:olefin) ratio of between 1:1 and 30:1, a olefin LHSV of about 0.3 to about 10 $hr^{-1}$, a temperature of about 100° to about 250° C. and pressures of about 1379 kPa g to about 6895 kPa g (about 200 to about 1000 psig). Further details on apparatus may be found in U.S. Pat. No. 4,870,222 which is incorporated by reference.

Alkylation of isoparaffins with olefins to produce alkylates suitable as motor fuel components is carried out at temperatures of −30° to 40° C., pressures from about atmospheric to about 6,895 kPa (1,000 psig) and a weight hourly space velocity (WHSV) of 0.1 to about 120. Details on paraffin alkylation may be found in U.S. Pat. No. 5,157,196 and U.S. Pat. No. 5,157,197, which are incorporated by reference.

The following examples are presented in illustration of this invention and are not intended as undue limitations on the generally broad scope of the invention as set out in the appended claims.

The structure of the UZM-44 zeolite of this invention was determined by x-ray analysis. The x-ray patterns presented in the following examples were obtained using standard x-ray powder diffraction techniques. The radiation source was a high-intensity, x-ray tube operated at 45 kV and 35 ma. The diffraction pattern from the copper K-alpha radiation was obtained by appropriate computer based techniques. Flat compressed powder samples were continuously scanned at 2° to 56° (2θ). Interplanar spacings (d) in Angstrom units were obtained from the position of the diffraction peaks expressed as θ where θ is the Bragg angle as observed from digitized data. Intensities were determined from the integrated area of diffraction peaks after subtracting background, "$I_o$" being the intensity of the strongest line or peak, and "I" being the intensity of each of the other peaks.

As will be understood by those skilled in the art the determination of the parameter 2θ is subject to both human and mechanical error, which in combination can impose an uncertainty of about ±0.4° on each reported value of 2θ. This uncertainty is, of course, also manifested in the reported values of the d-spacings, which are calculated from the 2θ values. This imprecision is general throughout the art and is not sufficient to preclude the differentiation of the present crystalline materials from each other and from the compositions of the prior art. In some of the x-ray patterns reported, the relative intensities of the d-spacings are indicated by the notations vs, s, m, w and vw which represent very strong, strong, medium, weak, and very weak respectively. In terms of 100×I/$I_o$, the above designations are defined as:

vw=<5; w=6-15; m=16-50; s=51-80; and vs=80-100

In certain instances the purity of a synthesized product may be assessed with reference to its x-ray powder diffraction pattern. Thus, for example, if a sample is stated to be pure, it is intended only that the x-ray pattern of the sample is free of lines attributable to crystalline impurities, not that there are no amorphous materials present.

In order to more fully illustrate the invention, the following examples are set forth. It is to be understood that the examples are only by way of illustration and are not intended as an undue limitation on the broad scope of the invention as set forth in the appended claims.

Example 1

5.28 g of NaOH, (97%) was dissolved in 111.88 g water. 1.16 g Al(OH)$_3$, (29.32 wt.-% Al), was added to the sodium hydroxide solution. Upon the mixture becoming a solution, 33.75 g Ludox AS-40 was added and the solution was stirred vigorously for 1-2 hours and then cooled to 0° C.-4° C. Separately, 8.89 g 1,5-dibromopentane, (97%) was mixed with 9.56 g 1-methylpyrrolidine, (97%) to form a second mixture. The second mixture was added to the cooled mixture to create the final reaction mixture. The final reaction mixture was vigorously stirred and transferred to a 300 cc stirred autoclave. The final reaction mixture was digested at 170° C. for 120 hours with stirring at 100 rpm. The product was isolated by filtration. The product was identified as UZM-44 by XRD. Analytical results showed this material to have the following molar ratios, Si/Al of 11.77, Na/Al of 0.21, N/Al of 1.02, C/N of 7.75. The product generated by this synthesis was calcined under flowing air at 600° for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 39.1% Si, 3.26% Al, 90 ppm Na with a BET surface area of 299 m$^2$/g, pore volume of 0.239 cm$^3$/g, and micropore volume of 0.139 cm$^3$/g.

Comparative Example 2

10.8 g of Aerosil 200 was added, while stirring, to a solution of 12.24 g 1,5-bis(N-methylpyrrolidinium)pentane dibromide in 114 g H$_2$O. A very thick gel was formed. Separately, a solution was made from 60 g H$_2$O, 3.69 g NaOH (99%), 0.95 g sodium aluminate (26.1% Al by analysis), and 1.86 g NaBr (99%). This second solution was added to the above mixture. The final mixture was divided equally between 7 45 cc Parr vessels. One vessel, which was digested for 12 days at 170° C. in a rotisserie oven at 15 rpm, yielded a product which was determined by XRD as having the IMF structure. The product was isolated by filtration. Analytical results showed this material to have the following molar ratios, Si/Al of 12.12, Na/Al of 0.08, N/Al of 1.03, C/N of 7.43. The product generated by this synthesis was calcined under flowing air at 600° for 6 hours. It was then ion exchanged four times with 1 M ammonium nitrate solution at 75° C. followed by a calcination at 500° C. under air for 2 hours to convert $NH_4^+$ into $H^+$. Analysis for the calcined, ion-exchanged sample shows 38.8% Si, 2.99% Al, 190 ppm Na with a BET surface area of 340 m$^2$/g, pore volume of 0.260 cm$^3$/g, and micropore volume of 0.160 cm$^3$/g.

Example 3

544 g of NaOH, (97%) was dissolved in 9.53 kg water. 118 g Al(OH)$_3$ was added to the sodium hydroxide solution while stirring. Of Ludox AS-40, 3.83 kg was added and the solution was stirred vigorously for 2 hours and then cooled to 0° C.-5° C. A solution containing 941 g H2O, 453 g 1,5-dibromopentane and 325 g N-methylpyrrolidine was added to the cooled mixture to create the final reaction mixture. The final reaction mixture was vigorously stirred and transferred to a 5 gallon stirred autoclave before digestion at 160° C. for 11 days. The product was isolated by filtration. The product was identified as UZM-44 by XRD. Analytical results showed this material to have the following molar ratios, Si/Al of 11.77, Na/Al of 0.21, N/Al of 1.02, C/N of 7.75. The product generated by this synthesis was calcined under flowing air at 600° for 6 hours. Analysis for the calcined sample shows a BET surface area of 301 m²/g, pore volume of 0.238 cm³/g, and micropore volume of 0.142 cm³/g.

Example 4

A UZM-44 in the H+ form was loaded into a vertical steamer. The UZM-44 was exposed to 100% steam at 725° C. for 12 hours or 24 hours. The starting UZM-44 had a BET surface area of 340 m²/g, pore volume of 0.301 cm³/g, and micropore volume of 0.154 cm³/g. After 12 hours of steaming, the UZM-44 was still identified as UZM-44 by XRD though the intensity of the first 3 peaks had increased to very strong, very strong—strong, and very strong—strong respectively. All other peaks were at positions and intensities described in Table B. The material had a BET surface area of 274 m²/g, pore volume of 0.257 cm³/g, and micropore volume of 0.127 cm³/g. After 24 hours of steaming, the UZM-44 was still identified as UZM-44 by XRD though the intensity of the first 3 peaks had increased to very strong, very strong—strong, and very strong—strong respectively. All other peaks were at positions and intensities described in Table B. The material had a BET surface area of 276 m²/g, pore volume of 0.262 cm³/g, and micropore volume of 0.128 cm³/g.

Example 5

UZM-44 was synthesized from a gel of composition 1 $Al_2O_3$: 43.6 $SiO_2$: 11.6 $Na_2O$: 6.52 1,5-dibromopentane: 18.95 N-methylpyrrolidine: 1321 $H_2O$ by dissolving NaOH in water and then liquid sodium aluminate was added to the sodium hydroxide solution. Ultrasil VN3 was then added as the silica source followed by 1,5-dibromopentane and N-methylpyrrolidine to form the final reaction mixture. The final reaction mixture was vigorously stirred and transferred to a 2 L stirred autoclave. The final reaction mixture was digested at 50° C. for 24 h then at 160° C. for 12 days while stirring. The product was isolated by filtration. The product was identified as UZM-44 by XRD. The product generated by this synthesis was calcined under flowing air at 600° for 6 hours. It was then ion-exchanged with 1 M ammonium nitrate solution.

Example 6

The product generated by the synthesis described in Example 1 was bound with $Al_2O_3$ in a 75:25 weight ratio and extruded in ⅛" cylinders to form UZM-44/$Al_2O_3$. The extrudates were then calcined using a 2° C./minute ramp to 550° C., holding for 3 hours and then cooling to room temperature. The 20 to 60 mesh fraction was isolated and then used as the catalytic composite in a chemical reaction to form ethylbenzene and xylenes.

Benzene and propane were fed at a 2:1 mole ratio into a reactor at 400 psig along with a hydrogen stream such that the hydrogen to hydrocarbon mole ratio was about 1.0. At 500° C. and 2.5 WHSV, conversion of benzene was 63 wt % and conversion of propane was 90 wt %. Yield of aromatic compounds at these conditions included 25 wt % to toluene, 1wt % to ethylbenzene, 7 wt % to xylenes and 5% to C9 aromatics.

The invention claimed is:

1. A hydrocarbon conversion process for the alkylation of aromatics comprising contacting an aromatic compound and an alkylating agent with a catalytic composite at hydrocarbon conversion conditions to give an alkylated aromatic product, the catalytic composite comprising a catalyst comprising a microporous crystalline zeolite, UZM-44-Modified, having a three-dimensional framework of at least AlO2 and SiO2 tetrahedral units and an empirical composition in the hydrogen form expressed by an empirical formula of

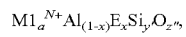

where M1 is at least one exchangeable cation selected from the group consisting of alkali, alkaline earth metals, rare earth metals, ammonium ion, hydrogen ion and combinations thereof, "a" is the mole ratio of M1 to (Al+E) and varies from about 0.05 to about 50, "N" is the weighted average valence of M1 and has a value of about +1 to about +3, E is an element selected from the group consisting of gallium, iron, boron, and combinations thereof, x is the mole fraction of E and varies from 0 to 1.0, y' is the mole ratio of Si to (Al+E) and varies from greater than about 9 to virtually pure silica and z" is the mole ratio of O to (Al+E) and has a value determined by the equation:

$$z''=(a \cdot N+3+4 \cdot y')/2$$

and is characterized in that it has the x-ray diffraction pattern having at least the d-spacings and intensities set forth in Table B:

TABLE B

| 2-Theta | d(t) | I/Io % |
|---|---|---|
| 7.71 | 11.47 | m-s |
| 8.84 | 10.00 | m-s |
| 9.24 | 9.56 | m |
| 11.76 | 7.52 | vw-w |
| 12.46 | 7.10 | m |
| 14.38 | 6.15 | vw |
| 14.64 | 6.05 | w |
| 15.26 | 5.80 | w |
| 15.52 | 5.70 | w-m |
| 16.58 | 5.34 | w |
| 17.72 | 5.00 | w-m |
| 18.64 | 4.76 | w |
| 22.56 | 3.94 | w-m |
| 23.06 | 3.85 | vs |
| 23.40 | 3.80 | s |
| 24.12 | 3.69 | m |
| 25.06 | 3.55 | m |
| 26.16 | 3.40 | vw-w |
| 26.74 | 3.33 | w-m |
| 28.82 | 3.10 | w-m |
| 30.12 | 2.96 | w |
| 35.86 | 2.50 | vw-w |
| 45.32 | 2.00 | w |
| 46.05 | 1.97 | vw-w |
| 46.92 | 1.93 | vw-w. |

2. The process of claim 1 further comprising removing an effluent comprising the alkylated aromatic product, fractionating the effluent, and recovering alkylated aromatic product.

3. The process of claim 2 further comprising subjecting the effluent to partial condensation and vapor-liquid separation prior to fractionation.

4. The process of claim 2 further comprising recycling at least a portion of the effluent to the catalyst.

5. The process of claim 1 wherein the hydrocarbon conversion process is alkylation of aromatics and the alkylated aromatic product is at least one linear alkyl substituted aromatic, and wherein the process is operated at an aromatic: olefin mole ratio of between 5:1 and 30:1, a LHSV of about 0.3 to about 6 hr$^{-1}$, a temperature of about 100° to about 250° C. and a pressures of about 200 to about 1000 psig.

6. The process of claim 1 wherein the catalyst is located in one or more catalyst zones arranged in series or parallel configuration, and wherein the catalyst may be in fixed beds or fluidized beds.

7. The process of claim 1 wherein the catalytic composite is thermally stable up to a temperature of greater than 600° C.

8. The process of claim 1 wherein the catalytic composite has a micropore volume as a percentage of total pore volume of less than 60%.

9. The process of claim 1 wherein the catalytic composite has micropore volume of less than 0.155 mL/g.

10. The process of claim 1 wherein the catalytic composite has micropore volume of less than 0.150 mL/g.

11. The process of claim 1 wherein the catalytic composite exhibits no feature at 200-300 Å on a dV/dlog D versus pore diameter plot of differential volume of nitrogen adsorbed as a function of pore diameter.

12. The process of claim 1 wherein the catalytic composite exhibits an adsorption feature occurring at greater than 450 Å on a dV/dlog D versus pore diameter plot of differential volume of nitrogen adsorbed as a function of pore diameter.

13. The process of claim 1 wherein the differential volume of nitrogen adsorbed by the catalytic composite at a pore diameter of 475 Å is greater than 0.1 mL $N_2$/gÅ on a dV/dlog D versus pore diameter plot of differential volume of nitrogen adsorbed as a function of pore diameter.

14. The process of claim 1 wherein the differential volume of nitrogen adsorbed by the catalytic composite at pore diameters greater than 475 Å is greater than 0.1 mL $N_2$/gÅ on a dV/dlog D versus pore diameter plot of differential volume of nitrogen adsorbed as a function of pore diameter.

\* \* \* \* \*